United States Patent
Fache et al.

(10) Patent No.: US 6,762,319 B1
(45) Date of Patent: Jul. 13, 2004

(54) HYDROCARBON, ALCOHOL AND/OR KETONE OXIDATION METHOD

(75) Inventors: Eric Fache, Caluire et Cuire (FR); Michel Costantini, Lyons (FR)

(73) Assignee: Rhodia Polyamide Intermediates, Saint-Fons (FR)

( * ) Notice: Subject to any disclaimer, the term of this patent is extended or adjusted under 35 U.S.C. 154(b) by 0 days.

(21) Appl. No.: 09/937,764

(22) PCT Filed: Mar. 29, 2000

(86) PCT No.: PCT/FR00/00786

§ 371 (c)(1),
(2), (4) Date: Apr. 16, 2002

(87) PCT Pub. No.: WO00/59858

PCT Pub. Date: Oct. 12, 2000

(30) Foreign Application Priority Data

Mar. 30, 1999 (FR) .............................................. 99 04203

(51) Int. Cl.⁷ ........................... C07C 51/16; C07C 51/31
(52) U.S. Cl. ....................... 562/527; 562/543; 562/418; 562/527; 562/539; 562/523; 554/134
(58) Field of Search .......................... 554/134; 562/418, 562/527, 536, 497, 523, 543; 502/66, 74

(56) References Cited

U.S. PATENT DOCUMENTS

| | | | | |
|---|---|---|---|---|
| 3,579,575 A | * | 5/1971 | Bouniot | 562/531 |
| 3,649,685 A | * | 3/1972 | Ishimoto et al. | 562/543 |
| 4,098,817 A | * | 7/1978 | Barone | 562/524 |
| 4,285,875 A | * | 8/1981 | Cornils et al. | 562/531 |
| 4,487,720 A | * | 12/1984 | Fruchey | |

FOREIGN PATENT DOCUMENTS

| | | | |
|---|---|---|---|
| EP | 0682000 | * | 11/1995 |
| EP | 0 870 751 | | 10/1998 |
| GB | 415 172 | | 8/1934 |
| GB | 942 415 | | 11/1963 |
| GB | 1 086 951 | | 10/1967 |
| GB | 1086951 | * | 10/1967 |
| WO | WO 96/31455 | * | 10/1996 |

OTHER PUBLICATIONS

Database WPI: Section CH, Week 199727, Derwent Pub., Ltd., London; Class A41, AN 1997–196571 XP002126081 & SU 982 319 (Monomers Res Des Intst) Nov. 10, 1996 (Abstract).

* cited by examiner

Primary Examiner—Alan L. Rotman
Assistant Examiner—Taylor V Oh
(74) Attorney, Agent, or Firm—Burns, Doane, Swecker & Mathis, L.L.P.

(57) ABSTRACT

The present invention relates to the oxidation, by means of oxygen or a gas containing it, of hydrocarbons to the corresponding carboxylic acids, alcohols and/or ketones or of alcohols and/or ketones to the corresponding carboxylic acids. It consists more precisely in a process for oxidizing hydrocarbon, alcohol and/or ketone, using oxygen or a gas containing it, in liquid phase and in the presence of a catalyst dissolved in the reaction medium, characterized in that the catalyst comprises a soluble manganese compound and at least one soluble chromium compound.

23 Claims, No Drawings

HYDROCARBON, ALCOHOL AND/OR KETONE OXIDATION METHOD

This application is a 371 of PCT/FR00/00786 filed Mar. 29, 2000.

The present invention relates to the oxidation, by means of oxygen or a gas containing it, of hydrocarbons to the corresponding carboxylic acids, alcohols and/or ketones or of alcohols and/or ketones to the corresponding carboxylic acids.

The direct oxidation using oxygen of hydrocarbons, more particularly cycloalkanes, in the presence of a catalyst is a process which has been the subject of study for a long time. Indeed, there would be obvious advantages in avoiding the use of an oxidizing agent such as nitric acid, as is used in one of the steps of the current industrial processes, which would do away with the need to treat the oxides of nitrogen that are generated.

In the numerous variants of a catalytic oxidation process of this kind using oxygen, cobalt is the catalyst most frequently recommended.

For instance, the American patent U.S. Pat. No. 2,223, 493, published in December 1940, describes the oxidation of cyclic hydrocarbons to the corresponding diacids in a liquid phase generally comprising acetic acid at a temperature of at least 60° C. with the aid of a gas containing oxygen and in the presence of an oxidation catalyst such as a cobalt compound.

The American patent U.S. Pat. No. 4,902,827, published in February 1990, describes an improvement to the air oxidation of cyclohexane to adipic acid in a liquid phase comprising acetic acid at a temperature of from 80° C. to 160° C. and in the presence of an oxidation catalyst comprising a soluble compound of cobalt and a soluble compound of zirconium and/or of hafnium.

More recently, the patent EP-A-0 694 333 has recommended the employment, in the context of the oxidation of hydrocarbons using oxygen, of a catalyst comprising a cobaltic salt and a ferric salt.

As another customary catalyst of this oxidation reaction mention may be made of manganese.

On economic grounds, and also to facilitate the purification of the resultant products, it is preferable to operate with the lowest possible catalyst concentration. Therefore, manganese is an advantageous catalyst in cyclohexane oxidation processes.

It is found, however, that the selectivities obtained with the catalyst systems used in the prior art processes described above are still in need of improvement.

The present invention aims to provide such improvement. It consists more precisely in a process for oxidizing hydrocarbon, alcohol and/or ketone, using oxygen or a gas containing it, in liquid phase and in the presence of a catalyst dissolved in the reaction medium, characterized in that the catalyst comprises at least one soluble manganese compound and at least one soluble chromium compound.

The hydrocarbons which are used as starting substrates in the process of the invention are more particularly alkanes, cycloalkanes, alkylaromatic hydrocarbons, alkenes and cycloalkanes having 3 to 20 carbon atoms.

Among these hydrocarbons the cycloalkanes, especially those which have a ring containing 5 to 12 carbon atoms, are without doubt the most important, since their oxidation leads to the dicarboxylic acids or to the intermediate cycloalkanols and cycloalkanones.

The hydrocarbon of greatest interest is cyclohexane, whose oxidation leads to adipic acid, one of the starting compounds for nylon 6,6, but which may also provide cyclohexanone, which leads to caprolactam and thus to nylon 6.

The present process can also be used for the oxidation of intermediate alcohols or ketones, especially cycloalkanols and cycloalkanones having 5 to 12 carbon atoms, to prepare the corresponding dicarboxylic acids. In the text below, the process will be more particularly described for the oxidation of hydrocarbons, essentially cycloalkanes, and, with special preference, for the oxidation of cyclohexane.

The catalyst system comprising compounds of manganese and of chromium makes it possible to prepare adipic acid directly with a good selectivity from the oxidation of cyclohexane; this feature is obviously highly advantageous.

The catalyst system comprises at least one manganese compound which is soluble in the reaction medium, selected for example, nonlimitatively, from manganese chloride, manganese bromide, manganese nitrate and manganese carboxylates such as manganese acetate tetrahydrate, manganese propionate, manganese adipate, manganese glutarate and manganese succinate.

The catalyst further comprises at least one chromium compound which is soluble in the reaction medium, selected for example, nonlimitatively, from chromium chloride, chromium bromide, chromium nitrate and chromium carboxylates such as chromium acetate, chromium propionate, chromium adipate, chromium glutarate and chromium succinate.

Finally, the catalyst may further comprise at least one compound of zirconium and/or of hafnium which is soluble in the reaction medium, selected for example, nonlimitatively, from zirconium chloride, zirconium bromide, zirconium nitrate and zirconium carboxylates such as zirconium acetate, zirconium propionate, zirconium adipate, zirconium glutarate and zirconium succinate and hafnium chloride, hafnium bromide, hafnium nitrate and hafnium carboxylates such as hafnium acetate, hafnium propionate, hafnium adipate, hafnium glutarate and hafnium succinate.

The molar ratios between the chromium and the manganese in the catalyst system can vary within wide limits. Thus it is possible to employ Cr/Mn molar ratios of advantageously between 0.00001 and 100, preferably between 0.001 and 10.

The amount of zirconium, when present, can vary within molar ratios, relative to the manganese, which are similar to those indicated above for chromium.

The catalyst can be obtained in situ by charging the manganese, chromium and, optionally, zirconium compounds to the reaction medium. It can also be prepared at the time of use by mixing the said compounds in the proportions necessary to obtain the desired Cr/Mn and, optionally, Zr/Mn molar ratios. This mixing is preferably carried out using a solvent, advantageously a solvent of the same kind as that used for the oxidation reaction, or directly in this solvent.

The amount of catalyst, expressed as a weight percentage of elemental manganese, chromium and, optionally, zirconium relative to the reaction mixture, is situated generally between 0.0001 and 5%, advantageously between 0.001 and 1%, although these values are not critical. What is important, however, is to have a sufficient activity but without using excessive amounts. The reason for this is that the catalyst will have to be separated from the final reaction medium and recycled.

It is advantageous to employ further an initiator compound for the oxidation reaction. The initiators are often hydroperoxides, such as for example cyclohexyl hydroperoxide or tert-butyl hydroperoxide. Further initiators are ketones or aldehydes, such as for example cyclohexanone, which is one of the compounds formed during the oxidation of cyclohexane or acetaldehyde. In general, the initiator represents from 0.01% to 20% by weight of the weight of the reaction mixture employed, although these proportions are not critical. The initiator is used above all at the time of starting the oxidation and when the oxidation of cyclohexane is carried out at a temperature lower than 120° C. It can be introduced from the beginning of the reaction.

The liquid reaction medium preferably contains an at least partial solvent for the carboxylic acid and/or alcohol and/or ketone which it is envisaged to prepare by employing the process of the invention. This solvent can be highly variable in nature, provided that it is not substantially oxidizable under the reaction conditions. It can be selected in particular from polar protic solvents and polar aprotic solvents. As polar protic solvents mention may be made, for example, of carboxylic acids having only primary or secondary hydrogen atoms, especially aliphatic acids having 2 to 9 carbon atoms, perfluoroalkylcarboxylic acids such as trifluoroacetic acid, and alcohols such as tert-butanol. As polar aprotic solvents mention may be made, for example, of lower alkyl (=alkyl radical having 1 to 4 carbon atoms) esters of carboxylic acids, especially aliphatic carboxylic acids having 2 to 9 carbon atoms, or of perfluoroalkylcarboxylic acids, tetramethylene sulphone (or sulpholane), acetonitrile, halogenated hydrocarbons such as dichloromethane, and ketones such as acetone.

Acetic acid is preferably used as solvent for the oxidation reaction of cyclohexane. It is judicious to employ a catalyst whose manganese and chromium constituents are in the form of compounds deriving from the carboxylic acid which is used as solvent, provided that the said compounds are soluble in the reaction medium. Acetates of manganese and of chromium are therefore used preferably, in particular for this reason.

The solvent, as defined above, represents generally from 1% to 99% by weight of the reaction medium, preferably from 10% to 90% and, more preferably, from 20% to 80%.

The oxidation can also be carried out in the presence of water introduced from the initial stage of the process.

The temperature at which the oxidation reaction is carried out is variable in accordance, in particular, with the substrate employed. It is generally between 50° C. and 200° C. and preferably between 80° C. and 140° C.

The pressure is not a critical parameter of the process. It can be lower than, equal to or greater than atmospheric pressure. In general, it will be situated between 0.1 MPa (1 bar) and 20 MPa (200 bar), although these values are not mandatory.

It is possible to use pure oxygen, air, oxygen-enriched or oxygen-depleted air, or else oxygen diluted with an inert gas.

The examples which follow illustrate the invention.

EXAMPLE 1, COMPARATIVE

A 125 ml titanium autoclave equipped with heating-collar heating means, a turbine, gas introduction means and pressure regulation means is charged with:

21.25 g (253 mmol) of cyclohexane 27.35 g of acetic acid 0.26 g (2.65 mmol) of cyclohexanone 0.0143 g (0.057 mmol of Co) of cobalt acetate tetrahydrate.

After closing the reactor, the mixture is stirred at 1000 revolutions per minute, air pressure is created (100 bar at 20° C.) and the mixture is heated. The temperature of the mixture reaches 105° C. in 10 minutes and this temperature is maintained for a further 170 minutes.

After cooling and depressurization, the reaction mixture consists of two liquid phases, which are homogenized by adding acetic acid.

The homogeneous mixture thus obtained is assayed by gas chromatography.

The results obtained are as follows:

degree of conversion (DC) of cyclohexane: <1%

This result demonstrates that cobalt is not a good catalyst at the concentration tested.

EXAMPLE 2, COMPARATIVE

Example 1 is repeated in the same apparatus and under the same operating conditions but replacing the cobalt acetate hydrate with 0.061 mmol of Mn in the form of manganese acetate tetrahydrate (0.015 g). The reaction time is 170 minutes.

The results obtained are as follows:

| | |
|---|---|
| Degree of conversion (DC) of cyclohexane: | 15.3% |
| DS for cyclohexanol relative to the cyclohexane converted: | 24.5% |
| DS for cyclohexanone relative to the cyclohexane converted: | 0.0% |
| DS for adipic acid relative to the cyclohexane converted: | 48.4% |
| DS for adipic acid + cyclohexanone + cyclohexanol relative to the cyclohexane converted: | 72.9% |
| DS for adipic acid + cyclohexanone + cyclohexanol relative to the cyclohexane converted: | |
| Adipic acid/total diacids formed molar ratio: | 77.6% |
| DS for other compounds (butyrolactone, valerolactone, hydroxyadipic acid, hydroxycaproic acid): | 13.2% |

EXAMPLE 3

Example 2 is repeated in the same apparatus and under the same operating conditions but adding to the catalyst 0.011 g of chromium acetate (0.04 mmol) of Cr.

| | |
|---|---|
| Degree of conversion (DC) of cyclohexane: | 11.3% |
| DS for cyclohexanol relative to the cyclohexane converted: | 10.2% |
| DS for cyclohexanone relative to the cyclohexane converted: | 0.0% |
| DS for adipic acid relative to the cyclohexane converted: | 65.5% |
| DS for adipic acid + cyclohexanone + cyclohexanol relative to the cyclohexane converted: | 75.7% |
| Adipic acid/total diacids formed molar ratio: | 78.9% |
| DS for other compounds: | 6.7% |

EXAMPLE 4

Example 2 is repeated in the same apparatus and under the same operating conditions but adding 0.0031 g of Cr acetate instead of 0.011 g.

| | |
|---|---|
| Degree of conversion (DC) of cyclohexane: | 13.4% |
| DS for cyclohexanol relative to the cyclohexane converted: | 16.2% |
| DS for cyclohexanone relative to the cyclohexane converted: | 0.0% |
| DS for adipic acid relative to the cyclohexane converted: | 58.5% |
| DS for adipic acid + cyclohexanone + cyclohexanol relative to the cyclohexane converted: | 74.7% |
| Adipic acid/total diacids formed molar ratio: | 79.0% |
| DS for other compounds: | 9.8% |

EXAMPLE 5

Example 3 is repeated in the same apparatus and under the same operating conditions but adding 15 ppm of Zr in the form of zirconium acetate. The reaction time is 60 minutes.

| | |
|---|---|
| Degree of conversion (DC) of cyclohexane: | 14.0% |
| DS for cyclohexanol relative to the cyclohexane converted: | 9.8% |
| DS for cyclohexanone relative to the cyclohexane converted: | 2.5% |
| DS for adipic acid relative to the cyclohexane converted: | 64.5% |
| DS for adipic acid + cyclohexanone + cycloexanol relative to the cyclohexane converted: | 76.8% |
| Adipic acid/total diacids formed molar ratio: | 78.7% |
| DS for other compounds: | 5.7% |

What is claimed is:

1. A process for oxidizing a hydrocarbon, an alcohol and/or a ketone to a carboxylic acid, comprising oxidizing the hydrocarbon, alcohol and/or ketone to the carboxylic acid using oxygen or a gas containing it, in liquid phase in a polar protic or polar aprotic solvent and in the presence of a catalyst dissolved in the reaction medium, wherein the catalyst comprises a soluble manganese compound and a soluble chromium compound, and wherein the catalyst does not contain cobalt.

2. The process according to claim 1, wherein the hydrocarbon is used as a starting substrate and comprises a cycloalkane having a ring containing 5 to 12 carbon atoms.

3. The process according to claim 1, wherein the alcohol and/or ketone used as a starting substrate is selected from the group consisting of cycloalkanols and cycloalkanones having a ring containing 5 to 12 carbon atoms.

4. The process according to claim 1, wherein the catalyst comprises at least one manganese compound which is soluble in the reaction medium, selected from the group consisting of manganese chloride, manganese bromide, manganese nitrate and manganese carboxylates.

5. The process according to claim 1, wherein the catalyst comprises at least one chromium compound which is soluble in the reaction medium, selected from the group consisting of chromium chloride, chromium bromide, chromium nitrate and chromium carboxylates.

6. The process according to claim 1, wherein the catalyst comprises a soluble zirconium or hafnium compound.

7. The process according to claim 6, wherein the soluble zirconium compound in the reaction medium is selected from the group consisting of zirconium chloride, zirconium bromide, zirconium nitrate and zirconium carboxylates.

8. The process according to claim 6, wherein the soluble hafnium compound in the reaction medium is selected from the group consisting of hafnium chloride, hafnium bromide, hafnium nitrate and hafnium carboxylates.

9. The process according to claim 1, wherein the molar-ratio between the chromium and the manganese is between 0.00001 and 100.

10. The process according to claim 1, wherein the amount of catalyst, expressed as a weight percentage of elemental manganese, elemental chromium and, optionally, elemental zirconium relative to the reaction mixture, is situated between 0.0001 and 5%.

11. The process according to claim 1, wherein the liquid reaction medium contains a solvent selected from the group consisting of aliphatic carboxylic acids having 2 to 9 carbon atoms, perfluoroalkylcarboxylic acids, alcohols, halogenated hydrocarbons, ketones, lower alkyl esters of carboxylic acids, and perfluoroalkylcarboxylic acids, tetramethylene sulphone, tetramethylene sulpholane and acetonitrile.

12. The process according to claim 1, wherein the solvent comprises acetic acid.

13. The process according to claim 1, wherein the solvent represents from 1% to 99% by weight of the reaction medium.

14. The process according to claim 1, wherein the temperature at which the oxidation reaction is carried out is between 50° C. and 200° C.

15. The process according to claim 1, wherein the pressure at which the oxidation reaction is carried out is between 0.1 MPa and 20 MPa.

16. The process according to claim 2, wherein the hydrocarbon is cyclohexane.

17. The process according to claim 3, wherein the starting substrate is cyclohexanol and/or cyclohexanone.

18. The process according to claim 4, wherein the catalyst is manganese acetate tetrahydrate, manganese propionate, manganese adipate, manganese glutarate or manganese succinate.

19. The process according to claim 5, wherein the catalyst comprises chromium acetate, chromium propionate, chromium adipate, chromium glutarate or chromium succinate.

20. The process according to claim 7, wherein the soluble zirconium compound is zirconium acetate, zirconium propionate, zirconium adipate, zirconium glutarate or zirconium succinate.

21. A process for oxidizing a hydrocarbon, an alcohol and/or a ketone to a carboxylic acid, comprising oxidizing the hydrocarbon, alcohol and/or ketone to the carboxylic acid using oxygen or a gas containing it, in liquid phase in a polar protic or polar aprotic solvent and in the presence of a catalyst dissolved in the reaction medium, wherein the catalyst consists essentially of a soluble manganese compound and a soluble chromium compound.

22. A process for oxidizing a hydrocarbon, an alcohol and/or a ketone to a carboxylic acid, comprising oxidizing the hydrocarbon, alcohol and/or ketone to the carboxylic acid using oxygen or a gas containing it, in liquid phase in a polar protic or polar aprotic solvent and in the presence of a catalyst dissolved in the reaction medium, wherein the catalyst consists of a soluble manganese compound and a soluble chromium compound.

23. A process for oxidizing a hydrocarbon, an alcohol and/or a ketone to a carboxylic acid, comprising oxidizing the hydrocarbon, alcohol and/or ketone to the carboxylic acid using oxygen or a gas containing it, in liquid phase in a polar protic or polar aprotic solvent and in the presence of a catalyst dissolved in the reaction medium, wherein the catalyst consists of a soluble manganese compound, a soluble chromium compound, and a soluble zirconium or hafnium compound.

* * * * *